(12) United States Patent
Makovec et al.

(10) Patent No.: US 8,258,185 B2
(45) Date of Patent: Sep. 4, 2012

(54) USE OF NEBOGLAMINE IN THE TREATMENT OF TOXICODEPENDENCY

(75) Inventors: Francesco Makovec, Lesmo (IT); Gianfranco Caselli, Milan (IT); Lucio Claudio Rovati, Monza (IT); Antonio Giordani, Pavia (IT)

(73) Assignee: Rottapharm S.p.A., Milan (IT)

( * ) Notice: Subject to any disclaimer, the term of this patent is extended or adjusted under 35 U.S.C. 154(b) by 0 days.

(21) Appl. No.: 13/192,071

(22) Filed: Jul. 27, 2011

(65) Prior Publication Data

US 2011/0288173 A1 Nov. 24, 2011

Related U.S. Application Data

(62) Division of application No. 12/067,390, filed as application No. PCT/IB2006/053603 on Oct. 3, 2006.

(30) Foreign Application Priority Data

Oct. 4, 2005 (IT) ............................. TO2005A0691

(51) Int. Cl.
*A61K 31/16* (2006.01)
*A61P 25/30* (2006.01)
*A61P 25/32* (2006.01)
*A61P 25/36* (2006.01)

(52) U.S. Cl. .................... 514/561; 562/507; 562/509

(58) Field of Classification Search .................... None
See application file for complete search history.

(56) References Cited

U.S. PATENT DOCUMENTS 5,523,323 A 6/1996 Maccecchini

FOREIGN PATENT DOCUMENTS

| EP | 0514023 | 4/1992 |
| WO | 94/20454 | 9/1994 |
| WO | 2005/115373 | 12/2005 |

OTHER PUBLICATIONS

Lanza et al Neuropharmacology, 1997, 36(8), 1057-1064.*
Bisaga et al. Exp. Opin. Invest. Drugs, 2000, 9(10), 2233-2248.*
Shin et al., Arch. Pharm. Res., 2003, 26, 1074-1078.*
Shepherd et al., Behavioural and pharmacological characterisation of the elevated "zero-maze" as an animal model of anxiety, Psychopharmacology (1994) 116:56-64.
Shin et al., Inhibitory Effects of Glycine on Morphine-Induced Hyperactivity, Reverse Tolerance and Postsynaptic Dopamine Receptor Supersensitivity in Mice, Arch Pharm Res, vol. 26, No. 12, 1074-1078, 2003.
Rockhold, Glutamatergic involvement in psychomotor stimulant action, Progress in Drug Research, vol. 50 (E. Jucker, Ed) 1998, pp. 157-192.
Garofalo et al., Cr 2249: A New Putative Memory Enhancer. Behavioural Studies on Learning and Memory in Rats and Mice, J. Pharm. Pharmacol. 1996, 48: 1290-1297.
Lanza et al., Characterization of a Novel Putative Cognition Enhancer Mediating Facilitation of Glycine Effect on Strychnine-Resistant Sites Coupled to NMDA Receptor Complex, Neuropharmacology, vol. 36, No. 8, pp. 1057-1064, 1997.
Lanza et al., Cognition Enhancing Profile of CR 2249, a New NMDA-Glycine Site Modulator, CNS Drug Reviews, vol. 3, No. 3, pp. 245-259, 1997 Neva Press, Branford, Connecticut.

* cited by examiner

*Primary Examiner* — Yevegeny Valenrod
(74) *Attorney, Agent, or Firm* — Roylance, Abrams, Berdo & Goodman, L.L.P.

(57) ABSTRACT

Use of neboglamine, (S)-4-amino-N(4,4-dimethyl-cyclohexyl)glutamic acid (CR 2249) (CAS Registry Number 163000-63-3), the racemic mixture thereof or a pharmaceutically acceptable salt thereof, for the preparation of a medicament for use in the treatment of toxicodependency induced by drugs such as CNS sedatives such as opiates, barbiturates, benzodiazepines, alcohol, stimulants such as amphetamines and cocaine, and hallucinogens such as LSD, mescalin, cannabis (marijuana) or fencyclidine.

10 Claims, No Drawings

USE OF NEBOGLAMINE IN THE TREATMENT OF TOXICODEPENDENCY

CROSS-REFERENCE TO RELATED APPLICATION

This application is a divisional application of Ser. No. 12/067,390, filed Mar. 19, 2008.

FIELD OF THE INVENTION

The present invention relates to a novel use of (S)-4-amino-N-(4,4-dimethylcyclohexyl)glutamic acid (CR 2249-neboglamine) (CAS Registry Number 163000-63-3), the racemic mixture thereof or a pharmaceutically acceptable salt thereof, for use in the treatment of toxicodependency induced by drugs such as Central Nervous System (CNS) sedatives such as opiates, benzodiazepines, barbiturates, alcohol, stimulants such as amphetamines and cocaine, and hallucinogens such as LSD, mescalin, cannabis (marijuana) or fencyclidine.

BACKGROUND OF THE INVENTION

The term "toxicodependency", whether physical or psychological, means the continued and totally implicit use of a drug. Such a use involves the risk of physical damage and the need to stop or limit the consumption of the substance, whether or not the drug taker is in agreement.

The term "psychological dependency" means an irresistible impulse (compulsion) to continue self-administering the drug in order to find pleasure. For certain drugs, the psychological dependency is the most important factor in their compulsive use.

The term "physical dependency" means a state of habituation to the drug accompanied by tolerance and that is manifested by abstinence syndromes.

Tolerance is the need to increase the dose of the drug in order to obtain the same effects as were initially obtained with lower doses; the abstinence syndrome is characterized by painful physical sensations that are manifested when the taking of the drug is stopped.

The substances commonly used by drug takers all induce psychological dependency, while others (the majority) also induce physical dependency.

The following groups may be distinguished: CNS sedatives such as opiates, benzodiazepines, barbiturates and alcohol, which also all induce physical dependency and tolerance; CNS stimulants, for instance amphetamine and cocaine which induce physical dependency to a minor extent, if at all; hallucinogens such as LSD, mescalin, cannabis (marijuana) and fencyclidine.

On the basis of published preclinical data, the compound neboglamine (CR 2249) has been shown to have significant modulatory properties on the glycine site (strychnine-insensitive) coupled to the NMDA receptor complex [Lanza et al., Neuropharmacology 36, 1057-64 (1997)], and also advantageous properties of promoting memory and learning in various animal models [Garofalo et al. J. Pharm. Pharmacol. 48, 1290-97 (1996)]. The facilitatory activity exerted by neboglamine on the NMDA receptor complex should be of therapeutic use in conditions of glutamatergic hypofunctionality.

It has been suggested that the NMDA receptor complex may be involved in a variety of functional responses to cocaine, for instance locomotor activity, dependency (continued reinforcement of self-administration), tolerance and toxicity (Rockhold R. W., Progress in Drug Research 50: 155-92, 1998).

It has also recently been demonstrated that glycine is capable of inhibiting the locomotor hyperactivity, tolerance and dependency induced by morphine in mice (K. W. Shin et al., Arch. Pharm. Res. 26: 1074-1078, 2003).

SUMMARY OF THE INVENTION

Thus, neboglamine was evaluated in animal experimental models that may be considered as predictive for the evaluation of toxicodependency induced by various drugs such as cocaine, morphine and benzodiazepines, which are widely representative of the syndromes caused by toxicodependency.

In the first model used, the inhibitory effect of neboglamine and glycine on the hypermotility induced by cocaine and morphine in rats was evaluated.

The motor activity was measured with a video camera and recorded using the Videotrack 512 system as described by Garofalo (J. Pharm. Pharmacol. 48: 1290-1297, 1996).

Physiological saline, neboglamine (30 mg/kg) or glycine (300 mg/kg) were administered via the i.p. route 30 minutes before physiological saline, morphine (10 mg/kg s.c.) or cocaine (20 mg/kg s.c.).

The locomotor activity was recorded for 15 minutes and the total distance covered (in cm) by the animal was recorded by the computer connected to the video camera. The results thus obtained are collated in Table 1.

TABLE 1

Inhibitory activity of neboglamine and glycine on the locomotor hyperactivity induced by cocaine and morphine

| Treatment | Dose (mg/kg) | Total distance (cm) | % increase vs. physiological saline | % inhibition vs. the drug (D) |
|---|---|---|---|---|
| Physiological saline (F) | F + F | 3300 | — | — |
| Neboglamine (N) | 30 + F | 3150 | (−)4.5 | — |
| Glycine (G) | 300 + F | 2900 | (−)12.1 | — |
| Cocaine (C) | F + 20 | 5800 | 75.7 | — |
| Morphine (M) | F + 10 | 5300 | 60.6 | — |
| N + C | 30 + 20 | 3600 | 9.1 | 88.0[(1)] |
| N + M | 30 + 10 | 3750 | 13.6 | 77.5[(1)] |
| G + M | 300 + 10 | 4250 | 28.8 | 52.5[(2)] |

[(1)] The % inhibition is calculated by the formula $\frac{[D - (D + N)]}{D - F} \times 100$

[(2)] The % inhibition is calculated by the formula $\frac{[D - (D + G)]}{D - F} \times 100$ From the data given in Table 1, it may be seen that both cocaine and morphine show a marked increase in locomotor activity (75.7% and 60.6%, respectively), whereas neboglamine and glycine do not significantly alter the spontaneous motility of the animal.

The motor activity accelerated by both the drugs cocaine and morphine is almost completely antagonized by doses of 30 mg/kg i.p. of neboglamine (88% and 77.5%, respectively). Glycine also inhibits the morphine-induced hyperkinetic activity, but with a smaller effect (52.5%) and at doses 10 times higher (300 mg/kg as opposed to 30 mg/kg of neboglamine).

In a second experiment, the capacity of neboglamine to inhibit the increased sensitivity (inverse tolerance) induced in rats was evaluated by chronic treatment with morphine.

Neboglamine (30 mg/kg) or physiological saline were administered via the i.p. route 30 minutes before morphine (10 mg/kg s.c.) for 6 days. On the seventh day, the test was performed, as described in the preceding experiment, in comparison with a group of animals treated with the same dose of morphine given acutely only on the 7th day (final day of the experiment). The results thus obtained are collated in Table 2.

TABLE 2

Inhibitory activity of neboglamine on the inverse tolerance induced by chronic treatment with morphine in rats

| Treatment | Dose (mg/kg) | Total distance (cm) | % increase vs. physiological saline | % inhibition of the hypersensitivity of morphine |
|---|---|---|---|---|
| Physiological saline (F) | — | 2800 | — | — |
| Morphine | 10 (s.c) | 5050 | 80.3 | 13 |
| Chronic morphine (MC) | 10 (s.c.) x 7 days | 6400 | 128.6 | — |
| CM + neboglamine (N) | 10 (s.c.) + 30 (N i.p.) x 7 days | 3850 | 37.5 | 70.8[(1)] |

[(1)]The % inhibition is calculated by the formula $\frac{[MC - (MC + N)]}{MC - F} \times 100$ Chronic treatment with morphine induces an increase in the motor activity of the rat, compared with the acute effect of the drug, by about 50% (128.6% as opposed to 80.3%). Chronic pre-treatment with neboglamine (30 mg/kg i.p for 7 days) succeeds in almost completely antagonizing (70.8%) the development of the inverse tolerance induced by the chronic treatment with morphine.

In a third experiment, we wished to study the effect of neboglamine both on the tolerance induced by a prolonged treatment with a benzodiazepine (diazepam) and on the abstinence crisis ("withdrawal") produced by stopping the chronic treatment with diazepam.

The experiment was performed in an elevated zero maze in accordance with the procedure described by Shepard et al. (Psychopharmacology 116: 56-64, 1994) with minor changes.

The rat, placed in one of the closed quadrants, had free access to all 4 of the quadrants (2 open and 2 closed) for a period of 5 minutes. A compound with anxiolytic activity produces a percentage increase in the time spent in the free quadrants.

In the acute studies, the compounds were administered via the s.c. route 30 minutes before the experiment, whereas in the tolerance and "withdrawal" experiments, they were administered via the s.c. route twice a day for 7 days and then retested 40 hours after the end of the chronic treatment. The results thus obtained are collated in Table 3.

TABLE 3

Effects of neboglamine on the tolerance and abstinence crisis induced by chronic treatment with diazepam in rats

| Treatment | Dose (mg/kg) s.c. | Time (seconds) spent in the open quadrants | % effect vs. controls (saline) |
|---|---|---|---|
| Physiological saline | — | 40 | 100.0 |
| Acute diazepam (D) | 5 | 105 | 262.5 |
| Chronic diazepam (D-C) | 5 x 2 | 58 | 145.0 |
| | (x7 days) + 5 (D) | | |
| Acute neboglamine (N) | 30 | 51 | 127.0 |
| Physiological (D-W) | — | 15 | 37.5 |
| Neboglamine+ (D-C) | 30 x 2 | 77 | 192.5 |
| | (x7 days) + 30 + 5 (D) | | |
| Neboglamine (D-W) | — | 44 | 110.0 |

Note:
Physiological (D-W) is the group treated with diazepam for 7 days and retested 40 hours later with physiological saline.
Neboglamine (D-W) is the group treated with diazepam and neboglamine for 7 days and retested 40 hours later with physiological saline 5 mg/kg s.c. of diazepam produce a significant anxiolytic effect (i.e. an increase in residence in the open quadrants): 262.5% compared with the control group.

The treatment continued for 7 days induces tolerance with a decrease in the anxiolytic effect from 262.5% to 145% compared with the control group. Neboglamine displays non-significant anxiolytic activity (127% compared with the controls). However, its co-administration with diazepam does not reduce tolerance (192.5% effect compared with the control). In addition, the co-administration of neboglamine was shown to inhibit the abstinence crisis induced by stoppage of the chronic treatment with diazepam [110% of effect for the group N-(D-W) as opposed to 37.5% of effect for the group (D-W)].

DETAILED DESCRIPTION OF THE INVENTION

In accordance with that presented above, a subject of the invention is pharmaceutical compositions comprising as active principle neboglamine or the racemic mixture thereof, in native form or pharmaceutically acceptable salts thereof.

Pharmaceutical formulations for using the compounds according to the invention may be prepared using conventional techniques. The formulations include those, suitable for oral use, for instance capsules, tablets, suspensions, emulsions, solutions; sterile solutions for parenteral use (including subcutaneous, intramuscular and intravenous administration), or preparations for topical or rectal use or other forms suitable for obtaining the desired therapeutic effect, for example solid formulations for oral use with delayed action, which allow a slow release of the active principle over time. Substances commonly used in the pharmaceutical field as excipients, binders, disintegrants and substances capable of stimulating transdermal absorption may be used together with the active principle in the pharmaceutical formulation.

Neboglamine compounds, such as the racemic mixture thereof, may thus be used in native form or as pharmaceutically acceptable salts. In the case of neboglamine, it is preferably the sodium or potassium salt or the hydrochloride.

The effective therapeutic amount of neboglamine to be used for the treatment of drug-induced toxicodependency should be between 10 and 600 mg and preferably from 30 to 300 mg per day of active principle, depending on the specific conditions of the treated patient, and the individual response to the treatment, the age and the weight of the patient.

What is claimed is:

1. A method for treating abstinence crisis induced by a drug selected from the group consisting of opiates and benzodiazepines, said method comprising administering to a patient in need thereof a therapeutically effective amount of a medicament comprising neboglamine, a racemic mixture thereof, or a pharmaceutically acceptable salt thereof.

2. A method for treating drug-induced tolerance induced by a drug selected from the group consisting of opiates and benzodiazepines, said method comprising administering to a patient in need thereof a therapeutically effective amount of a medicament comprising neboglamine, a racemic mixture thereof, or a pharmaceutically acceptable salt thereof.

3. The method according to claim 1, wherein said medicament also comprises pharmaceutically acceptable inactive ingredients selected from the group consisting of vehicles, binders, flavourings, sweeteners, disintegrants, preserving agents and humectants and mixtures thereof, or ingredients that facilitate the oral, parenteral, transdermal, transmucosal or rectal adsorption and that allow time-controlled release of active substances.

4. The method according to claim 1, wherein neboglamine is administered in a therapeutically effective amount of from 10 to 600 mg/day.

5. The method according to claim 1, wherein neboglamine is administered in a therapeutically effective amount of from 30 to 300 mg/day.

6. The method according to claim 1, wherein said drug is an opiate.

7. The method according to claim 1, wherein said drug is a benzodiazepine.

8. The method according to claim 1, wherein said medicament also comprises pharmaceutically acceptable inactive ingredients selected from the group consisting of vehicles, binders, flavourings, sweeteners, disintegrants, preserving agents and humectants and mixtures thereof, or ingredients that facilitate the oral, parenteral, transdermal, transmucosal or rectal adsorption and that allow time-controlled release of active substances.

9. The method according to claim 2, wherein said medicament also comprises pharmaceutically acceptable inactive ingredients selected from the group consisting of vehicles, binders, flavourings, sweeteners, disintegrants, preserving agents and humectants and mixtures thereof, or ingredients that facilitate the oral, parenteral, transdermal, transmucosal or rectal adsorption and that allow time-controlled release of active substances.

10. A method for treating toxicodependency induced by drugs selected from the group consisting of opiates and benzodiazepines, said method comprising administering to a patient in need thereof a therapeutically effective amount of a medicament comprising neboglamine, (S)-4-amino-N(4,4-dimethylcyclohexyl)glutamic acid (CR 2249) (CAS Registry Number 163000-63-3), a racemic mixture thereof, or a pharmaceutically acceptable salt thereof.

* * * * *